US012180532B2

(12) United States Patent
Pierquin

(10) Patent No.: US 12,180,532 B2
(45) Date of Patent: Dec. 31, 2024

(54) METHOD AND DEVICE FOR DETECTING AT LEAST ONE MICROORGANISM ACCORDING TO THE STAINING KINETICS THEREOF, AND DETECTION SUPPORT

(71) Applicant: REDBERRY, Illkirch-Graffenstaden (FR)

(72) Inventor: Joseph Pierquin, Molsheim (FR)

(73) Assignee: REDBERRY, Illkirch-Graffenstaden (FR)

( * ) Notice: Subject to any disclaimer, the term of this patent is extended or adjusted under 35 U.S.C. 154(b) by 617 days.

(21) Appl. No.: 17/279,162

(22) PCT Filed: Oct. 4, 2019

(86) PCT No.: PCT/EP2019/076869
§ 371 (c)(1),
(2) Date: Mar. 24, 2021

(87) PCT Pub. No.: WO2020/070265
PCT Pub. Date: Apr. 9, 2020

(65) Prior Publication Data
US 2021/0277440 A1 Sep. 9, 2021

(30) Foreign Application Priority Data
Oct. 5, 2018 (FR) ...................................... 18/59253

(51) Int. Cl.
*G06K 9/00* (2022.01)
*C12Q 1/04* (2006.01)
(Continued)

(52) U.S. Cl.
CPC .............. *C12Q 1/04* (2013.01); *G06T 7/0014* (2013.01); *H04N 23/56* (2023.01);
(Continued)

(58) Field of Classification Search
CPC ........ C12Q 1/04; C12Q 1/06; G01N 15/1475; G01N 2021/6439; G01N 1/30;
(Continued)

(56) References Cited

U.S. PATENT DOCUMENTS

2003/0082516 A1* 5/2003 Straus ................ G01N 21/6428
435/287.1
2006/0050946 A1* 3/2006 Mitchison ............. G06T 7/0012
382/133
(Continued)

FOREIGN PATENT DOCUMENTS

| EP | 0 713 087 A1 | 5/1996 |
|---|---|---|
| WO | WO 2009/091402 A1 | 7/2009 |
| WO | WO 2017/146648 A1 | 8/2017 |

OTHER PUBLICATIONS

Bean et al., "Development of Ultra-High-Density Screening Tools for Microbial "Omics"", PLOS ONE, Jan. 21, 2014, total 8 pages.
(Continued)

*Primary Examiner* — Atiba O Fitzpatrick
(74) *Attorney, Agent, or Firm* — Birch, Stewart, Kolasch & Birch, LLP

(57) ABSTRACT

A method for detecting, on a detection support, at least one microorganism present in a sample to be analysed and revealed by means of at least one cell marker includes a first taking of an image ($I_0$, $I'_0$) before a step of controlled release of said marker and bringing this marker into contact with said microorganism, and at least one taking of an image ($I_i$) following this contact step, so as to detect said microorganism according to the change in the staining kinetics thereof, by means of a comparative analysis between the different images that have been taken. An automated detection device is capable of implementing the method and a detection support is capable of being used in the method and which is part of the device.

27 Claims, 4 Drawing Sheets

Figure 1:
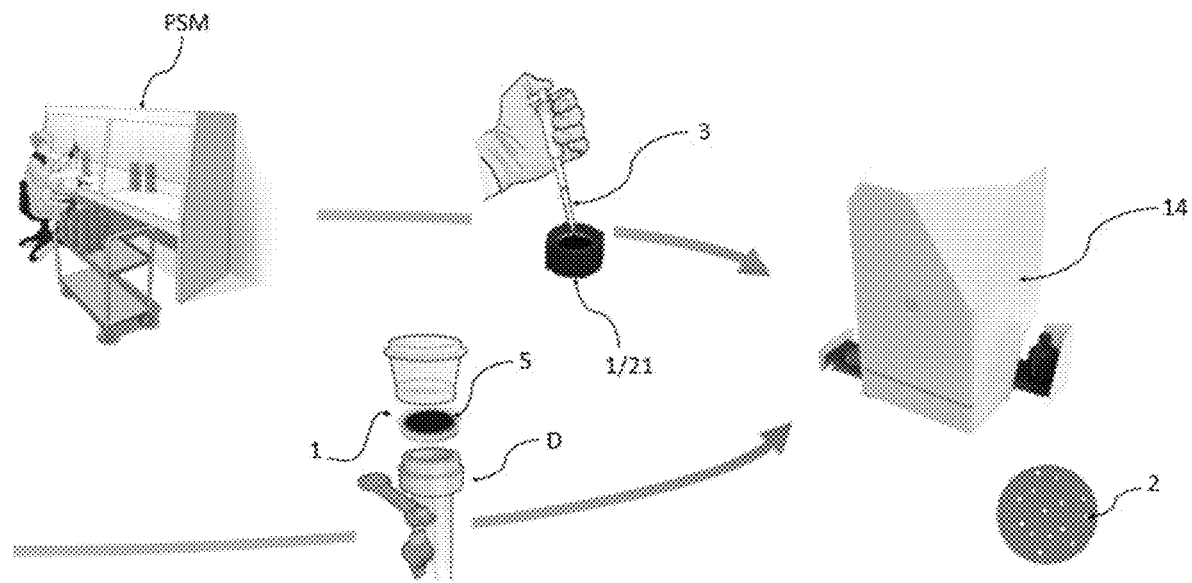

(51) Int. Cl.
*G06T 7/00* (2017.01)
*H04N 23/56* (2023.01)

(52) U.S. Cl.
CPC ............ *G06T 2207/10056* (2013.01); *G06T 2207/10064* (2013.01); *G06T 2207/30024* (2013.01); *G06T 2207/30204* (2013.01); *G06T 2207/30242* (2013.01)

(58) Field of Classification Search
CPC ....... G01N 2001/302; G01N 2001/305; G01N 2001/307; G01N 1/31; G01N 1/312; G01N 2001/315; G01N 2001/317; G01N 2015/1486; G06T 2207/10056; G06T 2207/30024; G06T 2207/10061; G06T 7/0014; G06T 7/0016; G06T 2207/30204; G06T 2207/10064; G06T 2207/30242; G06V 20/69–698; G06V 2201/04; B01L 2200/026; B01L 2200/027; C12M 23/16
See application file for complete search history.

(56) References Cited

U.S. PATENT DOCUMENTS

| | | | |
|---|---|---|---|
| 2006/0073470 A1* | 4/2006 | Noda | C12Q 1/04 435/4 |
| 2006/0246535 A1 | 11/2006 | Burns et al. | |
| 2008/0176273 A1 | 7/2008 | Eden et al. | |
| 2016/0160169 A1* | 6/2016 | Paczkowski | G01N 33/543 506/10 |
| 2018/0028079 A1* | 2/2018 | Gurevich | A61B 5/7232 |
| 2018/0043357 A1* | 2/2018 | Bocchi | B01L 3/50273 |
| 2019/0011882 A1* | 1/2019 | Gusyatin | C12M 41/36 |
| 2019/0287244 A1* | 9/2019 | Wakui | C12M 41/36 |
| 2019/0384962 A1* | 12/2019 | Hayut | G06V 20/693 |
| 2021/0149174 A1* | 5/2021 | Levenson | G02B 21/16 |
| 2021/0264595 A1* | 8/2021 | Plesch | G01N 21/6428 |
| 2022/0066390 A1* | 3/2022 | Gusyatin | G03H 1/10 |

OTHER PUBLICATIONS

Čepl et al., "Patterning of mutually interacting bacterial bodies: close contacts and airborne signals", BMC Microbiology, 2010, vol. 10, No. 139, total 15 pages.

Choi et al., "Integrated micro-optofluidic platform for real-time detection of airborne microorganisms", Scientific Reports, Nov. 2, 2015, vol. 5, No. 15983, total 10 pages.

Ferrari et al., "Multistage Classification for Bacterial Colonies Recognition on Solid Agar Images". 2014 IEEE International Conference on Imaging Systems and Techniques (IST) Proceedings, IEEE, Oct. 14, 2014, pp. 101-106.

Herricks et al., "One-Cell Doubling Evaluation by Living Arrays of Yeast, ODELAY!", G3. Genes|Genomes|Genetics, Jan. 2017, vol. 7, pp. 279-288.

Højris et al., "A novel, optical, on-line bacteria sensor for monitoring drinking water quality", Scientific Reports, Apr. 4, 2016, vol. 6, No. 23935, total 10 pages.

International Search Report, issued in PCT/EP2019/076869, dated Nov. 19, 2019.

Jeanson et al., "Spatial Distribution of Bacterial Colonies in a Model Cheese", Applied and Environmental Microbiology, Feb. 2011, vol. 77, No. 4, pp. 1493-1500.

Jung et al., "Real-time bacterial microcolony counting using on-chip microscopy", Scientific Reports, Feb. 23, 2016, vol. 6, No. 21473, total 8 pages.

Levin-Reisman et al., "ScanLag: High-throughput Quantification of Colony Growth and Lag Time", Journal of Visualized Experiments, Jul. 15, 2014, vol. 89, No. e51456, total 15 pages.

Puchkov, "Image Analysis in Microbiology: A Review", Journal of Computer and Communications, Nov. 28, 2016, vol. 4, pp. 8-32.

* cited by examiner

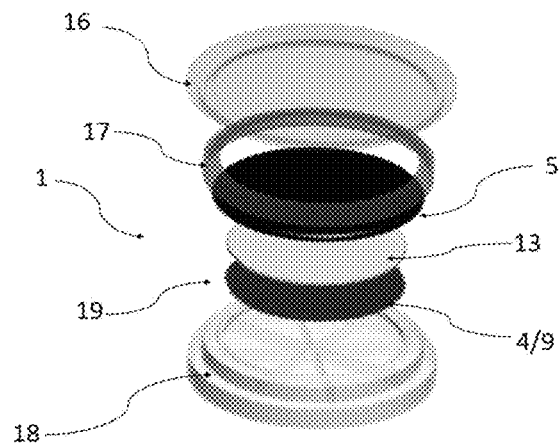
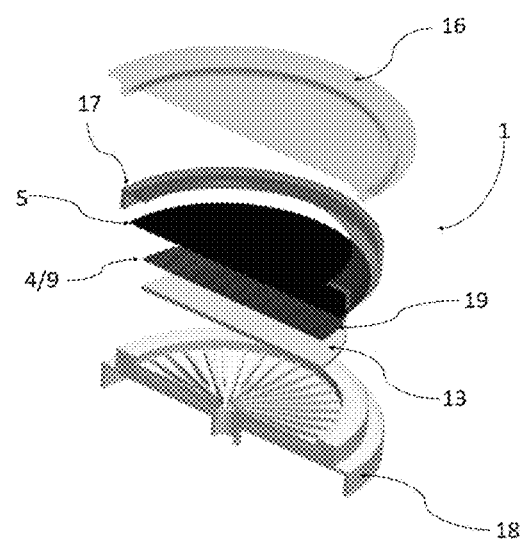
FIG. 3A
FIG. 3B
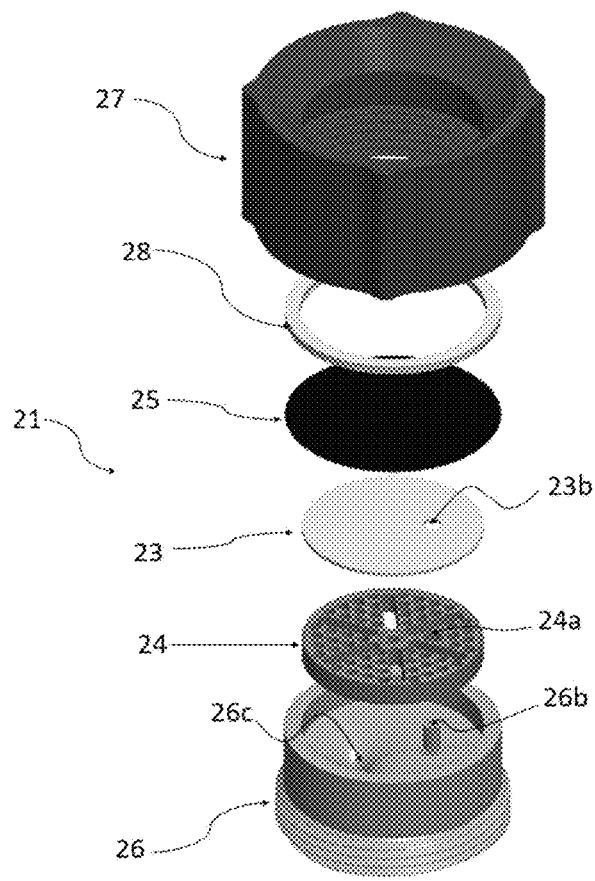
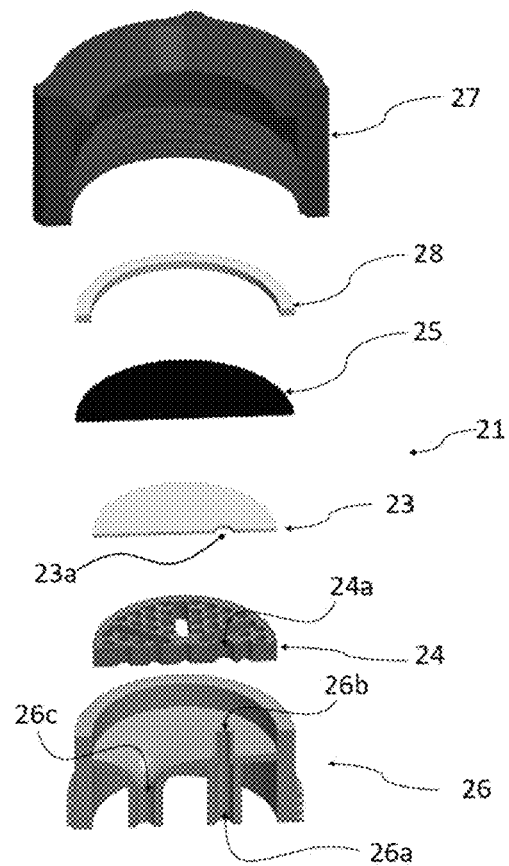
FIG. 4A
FIG. 4B

METHOD AND DEVICE FOR DETECTING AT LEAST ONE MICROORGANISM ACCORDING TO THE STAINING KINETICS THEREOF, AND DETECTION SUPPORT

The present invention relates to the field of detecting microorganisms such as bacteria, yeast and mould type in the solid phase.

The present invention is mainly applicable to the field of industrial microbiology, for example, but not limited to, the pharmaceutical, biotechnological, cosmetic or food-processing industries, or for clinical or environmental microbiology.

The invention more particularly relates to a device and a method for the very early detection of microorganisms in the solid phase on suitable supports, without the need to cultivate said microorganisms for the multiplication thereof.

Numerous techniques are currently implemented to detect contaminants, such as bacteria, in a sample to be tested.

The oldest and most conventional method consists of depositing a sample, optionally after filtering, on the surface of a nutrient agar growth medium, which can be more or less selective for one or more type(s) of microorganisms.

Said medium is then incubated at the appropriate temperature for growing the desired microorganism, often for up to several days, before an operator "manually" counts the colonies visible to the naked eye.

Such a method, although highly sensitive and allowing a single viable and cultivable contaminant to be detected in the original sample, has the drawback of requiring a relatively long incubation period to allow colonies that have formed on the agar to be detected by the naked eye.

Instead of a solid agar, another possibility involves inoculating a liquid medium in which microbial growth will be detected, after incubation, by turbidimetry for example, whereby the measured absorbance is proportional to the concentration of microorganisms present in the medium.

The drawback of liquid-phase detection techniques is that they do not detect microbial concentrations below $10^6$ or $10^7$ cells/mL. Thus, the sample must be incubated again for a variable period of time in order to reach such a cell concentration.

It should also be noted that certain microorganisms, under the effect of stress, for example thermal stress, or as a result of the presence of inhibiting agents in a sample, can take a particularly long time to multiply, thus further prolonging the moment in time when they will be detectable using conventional cultivation techniques.

Another known method in the prior art involves carrying out a polymerase chain reaction, also known as PCR amplification, to determine the presence of specific microorganisms in a sample, by amplification of a DNA or RNA sequence.

However, these methods have the drawback of requiring a plurality of strands of nucleic acid, i.e. a plurality of contaminating microorganisms in a sample, and generally at least several tens of microorganisms. Such methods are thus less sensitive than conventional cultivation techniques based on microbial growth.

Thus, many methods have been developed and perfected in recent years in order to increase the speed of detecting microorganisms while trying to maintain the sensitivity of conventional growth-based techniques.

Most of these methods are based on detecting the fluorescence emitted by specific fluorescent chemical substances, fluorophores or fluorochromes, which are coupled, by different staining techniques, to cellular functions or structures (nucleic acids, proteins, enzymes etc.) of the microorganisms to be detected.

These methods require the implementation of specific detection devices, such as microscopes for the "DEFT" (Direct Epifluorescence Filter Technique) or cytometers.

Thus, the technique of flow cytometry is now commonly used to detect and count microorganisms present in a sample.

In this technique, cells or particles, which can be stained with a fluorophore and suspended in a liquid, are isolated one after the other in the form of a single-cell stream. They are then passed, one by one and at a high speed, through a light source, for example a light beam from a laser.

The light diffused and emitted by the cells, which is fluorescent in the case of staining with a fluorophore after excitation thereof at a given wavelength, is directed by a system of mirrors and filters constituting the optical device of the cytometer, towards a set of light detectors. These detectors in particular incorporate photomultiplier tubes which will convert the light signals into electrical signals that can then be analysed by a computer to generate data regarding, for example, the physical features of the cells.

The flow cytometers currently available commercially are capable of analysing several hundred of cells, or "events" per second, in real time, and some of these appliances can be configured to allows cells or particles to be sorted as a function of the optical properties thereof.

However, the detection of rare events is often complicated, whether implementing flow cytometry or the microscopic technique.

Indeed, flow cytometry has a limited sensitivity, which is estimated, in the best-case scenario, to be between $10^2$ and $10^3$ cells/mL of suspension, and is matrix-dependent.

In the "DEFT" technique, a sample to be analysed is filtered through a membrane retaining the microorganisms liable to be contained in said sample.

The microorganisms are then stained with a fluorochrome, for example acridine orange, which interacts with the DNA or the RNA, and are then counted by visual analysis of a plurality of fields of the membrane using an epifluorescence microscope.

In the case of fluorescent microscopy, it is estimated that at least $10^4$ cells must be present on a membrane having a diameter of 25 mm, in order to obtain representative results, bearing in mind that the counting is carried out only on a small part of the membrane (less than 10% of the total size), and that a homogeneous distribution of cells is assumed and not certain.

However, in some applications in industrial or clinical microbiology, early detection of the presence of a single contaminant or of a few contaminants in a sample can be particularly important. Indeed, the products manufactured and/or transformed in this type of industry are particularly sensitive, in particular as a result of the ultimate purpose thereof (food, consumer health, etc.). Ensuring, as quickly as possible, the irreproachable microbiological quality thereof is thus essential, or, if this is not the case, it is essential to be able to quickly identify the source of the contamination.

The solid-phase cytometry method, also known as laser scanning cytometry, was developed in recent years in particular for these reasons, and is applicable to filterable samples. It is in particular the subject-matter of the European patent document EP 0 713 087.

In this method, after a first step of filtering a sample on a suitable membrane, any microorganisms potentially present on said membrane are subjected to a staining step using a fluorophore.

The entire surface of the membrane is then scanned by a laser beam to excite the fluorophore and count any microorganisms potentially present and viable in the original sample to be analysed, by measuring the fluorescence emitted.

The device, known as ChemScan RDI (registered trademark), implements this solid-phase cytometry method.

However, the devices currently available commercially to implement the solid-phase cytometry technique, as well as the necessary reagents, are particularly expensive and require significant investments. As a result, this technique is not accessible to all laboratories.

Moreover, once the detection and enumeration of the microorganisms has been carried out, the toxic effects of the reagents used on the cellular metabolism are capable of preventing subsequent cultivation for identifying said microorganisms.

It should also be noted that this solid-phase cytometry method is only applicable to filterable matrices, and that the time required, from depositing the sample on a solid support until the results are obtained with the enumeration of the microorganisms present on said solid support, is relatively long; the time required is indeed estimated to be at least 90 minutes and can reach up to 4 hours, depending on the application.

Finally, whether using the flow cytometry technique or the solid-phase cytometry technique, the rate of false positives detected remains relatively high. Indeed, inert particles, for example dust, that are not microorganisms, are also liable to emit a natural fluorescence, or even combine with the fluorochrome to emit an interfering florescence.

This constitutes a real drawback of the existing methods insofar as, depending on the fields of application, a sample that proves to be a false positive will require further investigations, which are costly in terms of time and which can also have significant financial repercussions, particularly if a production line (for example, for biopharmaceuticals) has to be shut down for the duration of said investigations.

In general, the methods implementing cell staining with a fluorophore require the sample to be handled by qualified personnel, as well as the fluorescent reagent to be handled and brought into contact with the microorganisms to be detected, which inevitably creates a risk of contaminating said sample.

It should also be noted that all of these operations, as well as the work carried out upstream of sample preparation, in particular including filtration, activation, staining and washing, etc., inevitably require a significant amount of handling time by an operator, which equally delays the moment at which a potential contamination is detected.

The invention provides the possibility of overcoming, at least in part, the various aforementioned drawbacks of the prior art by proposing a method and a device for the extremely early, almost instantaneous where necessary, detection of the one or more microorganism(s) potentially present in an original sample to be analysed.

The method and the device of the invention are based on detecting and analysing the staining kinetics of potential microorganisms by means of a cell marker delivered in a controlled manner and without time-consuming manual operation that is in particular liable to cause contamination of the sample.

For this purpose, the present invention relates to a method for detecting, on a solid detection support, at least one microorganism, of the bacteria, yeast or mould type, present in a sample to be analysed and revealed by means of at least one cell marker, said method including at least the following steps, in this order:

a) Depositing said sample to be analysed on said solid detection support;

b) Illuminating said detection support at least once with light radiation capable of revealing said at least one cell marker;

c) Acquiring at least one image $I_0$ in a first phase $P_0$ of said sample on at least one portion of said detection support by means of an optical imaging device targeting a field of view that is at least 10 mm long by at least 10 mm wide;

d) Carrying out a controlled release of said at least one cell marker, through the detection support, to bring said marker into contact with said microorganism;

e) Acquiring, by means of said optical device, an image $I_i$ ($i \geq 1$) of each portion of the detection support of which an image was acquired at $P_0$ in at least one subsequent phase $P_i$ after the step of the controlled release of said marker so as to detect said at least one microorganism according to the change in the staining kinetics of said microorganism;

f) Carrying out a comparative analysis, per portion of the detection support, between said image $I_0$ acquired at $P_0$ and each image I acquired in at least one subsequent phase $P_i$ and drawing a conclusion as regards the presence or absence of at least one microorganism in said sample.

Preferably, said detection support is illuminated locally with light radiation every time an image is acquired at $P_0$, $P_i$.

In one particularly advantageous example embodiment, the method of the invention includes at least the following steps, in this order:

a1) Depositing said sample to be analysed on said solid detection support;

b1) Illuminating locally said detection support by light radiation capable of revealing said at least one cell marker;

c1) Simultaneously with the illumination step b1), acquiring at least one image $I_0$, $I'_0$ in a first phase $P_0$ of said sample on at least one portion of said detection support by means of an optical imaging device targeting a field of view that is at least 10 mm long by at least 10 mm wide;

d1) Carrying out a controlled release of said at least one cell marker, through the detection support, to bring said marker into contact with said microorganism;

e1) Within a lapse of time of less than 5 seconds after step d1) of the controlled release of said cell marker, illuminating locally said detection support with said light radiation capable of revealing said at least one cell marker;

f1) Simultaneously with the illumination step e1), acquiring an image $I_1$, $I'_1$, by means of said optical device, of each portion of the detection support of which an image was acquired at $P_0$ in at least one subsequent phase $P_1$ after the step of the controlled release of said marker;

g1) Re-illuminating locally, at least once, said detection support with said light radiation;

h1) Simultaneously with the illumination step g1), acquiring an image $1_2$, $I'_2$, by means of said optical device, of each portion of the detection support of which an image was acquired at $P_0$ and at $P_1$ in at least one second subsequent phase $P_2$ in order to detect said at least one microorganism according to the change in the staining kinetics of said microorganism;

i1) Carrying out a comparative analysis, per portion of the detection support, between said image $I_0$, $I'_0$ acquired at $P_0$ and said images $I_1$, $I'_1$; $I_2$, $I'_2$ acquired in at least two subsequent phases $P_1$ and $P_2$ and drawing a conclusion as regards the presence or absence of at least one microorganism in said sample.

According to particular and non-limiting features of the method of the invention:
  the detection support is subjected to n displacements along distinct paths with a view to spatially dividing said detection support into n+1 portions, images whereof are acquired in at least two phases $P_0$ and $P_i$, where n is an integer less than or equal to 20;
  an optical imaging device having a resolution at least equal to 20 megapixels, preferably more than 100 megapixels, is used in the image acquisition steps c) and e) or c1), f1) and h1);
  if it is concluded that at least one microorganism is present in said sample in step f) or i1), an enumeration of the microorganisms present in said sample is carried out;
  said cell marker is a fluorescent marker;
  said cell marker released in a controlled manner in step d) or d1) is encapsulated in an encapsulation means in solid form, for example in the form of a powder, and said detection support comprises a solvent for dissolving said marker;
  said cell marker is encapsulated in an encapsulation means in liquid form;
  said encapsulation means is heat-sensitive and, in step d) or d1), a controlled release of the cell marker encapsulated in said heat-sensitive encapsulation means is carried out by subjecting the latter to a temperature rise capable of melting said heat-sensitive encapsulation means, for example by increasing the temperature from ambient temperature to a maximum temperature of 45° C.;
  the cell marker in a liquid solution is conveyed, in a controlled manner, to the solid detection support containing the sample to be analysed;
  a volume comprised between 10 and 2,000 μL of said sample to be analysed is deposited directly on said detection support;
  said sample to be analysed is filtered through a filtering membrane having a cut-off threshold comprised between 0.2 and 0.45 μm, preferably a cut-off threshold equal to 0.3 μm, said filtering membrane being positioned directly in said detection support;

The present invention further relates to a method for distinguishing microorganisms from dust on the detection supports having received the samples to be analysed, characterised by:
  measuring, after each image acquisition, the brightness of the luminescent pixels or clusters of pixels detected;
  comparing the brightness of each luminescent pixel or cluster of pixels detected in the different images;
  identifying the pixels or clusters of pixels having a brightness that does not substantially change in at least two consecutive images during the staining kinetics;
  analysing and counting the pixels or clusters of pixels having a brightness that changes during the staining kinetics.

The invention further relates to a device for detecting at least one microorganism, of the bacteria, yeast or mould type, present in a sample to be analysed, capable of implementing the detection method of the invention, and comprising at least:
  a solid detection support intended to receive said sample to be analysed which is liable to contain at least one microorganism;
  a means of storing at least one cell marker of said microorganism;
  a means for the controlled release of said cell marker to bring said marker into contact with said sample to be analysed;
  a means of illuminating said detection support;
  an optical device for acquiring images of at least one portion of said detection support, said optical device having a field of view that is at least 10 mm long by at least 10 mm wide;
  means for storing in memory, for comparing and for analysing the images acquired by the optical device so as to detect said at least one microorganism potentially present in said sample according to the change in the staining kinetics of said at least one microorganism.

Preferably, the device of the invention comprises means for displacing said detection support beneath said optical imaging device.

Advantageously, in the detection device of the invention:
  said solid detection support includes at least one filtering membrane resting on a glass fibre support disc;
  said means for storing the cell marker is included in the detection support and consists of a layer of microcapsules formed by said cell marker encapsulated in an encapsulation means, said layer of microcapsules being disposed between said glass fibre support disc and said filtering membrane; in such a case, said means for the controlled release of the cell marker includes heating means and temperature control and regulation means capable of producing a temperature rise inside the device and of melting said encapsulation means encapsulating the cell marker;
  said cell marker storage means consists of a reserve of liquid cell marker solution separate from the detection support and said detection device comprises means for conveying said cell marker from said storage means to said detection support; in such a case, said means for the controlled release of the cell marker can include at least one controlled-flow pump;
  said optical imaging device has a depth of focus in the order of or equal to 0.5 mm;
  said optical imaging device is based on a CMOS sensor camera,
  said optical imaging device has a field of view of 25 mm*25 mm;
  said optical imaging device has a resolution at least equal to 20 megapixels and preferably greater than 100 megapixels.

The invention further relates to a detection support capable of being implemented in the detection method according to the invention or forming part of the composition of the detection device according to the invention and consisting, at least, of a rigid base through which passes at least one liquid feed line and at least one liquid aspiration and discharge line, said feed line being extended by a vent projecting from said base and passing through, on the one hand, a first orifice made in a rigid and permeable support means above said base and, on the other hand, a second orifice made in a flexible support disc made of glass fibres, said disc being positioned on said rigid and permeable support means and supporting a filtering membrane having a cut-off threshold comprised between 0.2 and 0.45 μm, capable of retaining microorganisms, said detection support further comprising a clamping ring fixed such that it is integral with said base and holding said base, said rigid and permeable support means, said support disc and said filtering membrane together.

The present invention has numerous advantages. On the one hand, the present method, which is based on the assessment of the staining kinetics of microorganisms, makes it possible to almost immediately detect, within minutes or tens of minutes at most after preparing a sample, and without the need for cultivation, the presence or the absence of one or more living microorganisms in said sample, while discriminating, in an extremely reliable manner, between these microorganisms and potential artefacts, such as dust or the like.

On the other hand, the invention only requires the sample to be handled very little, and in any case does not require the cell marker to be handled at all, which operation is complex, requires qualified personnel and creates a non-negligible risk of contaminating said sample.

Figure 2:
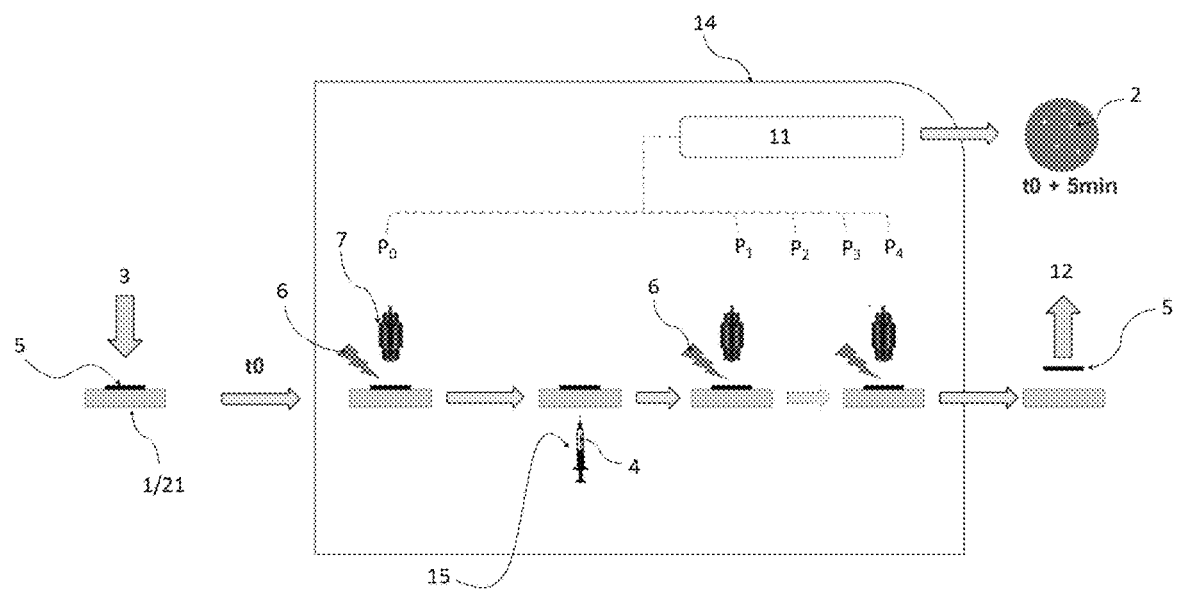
Figure 5:
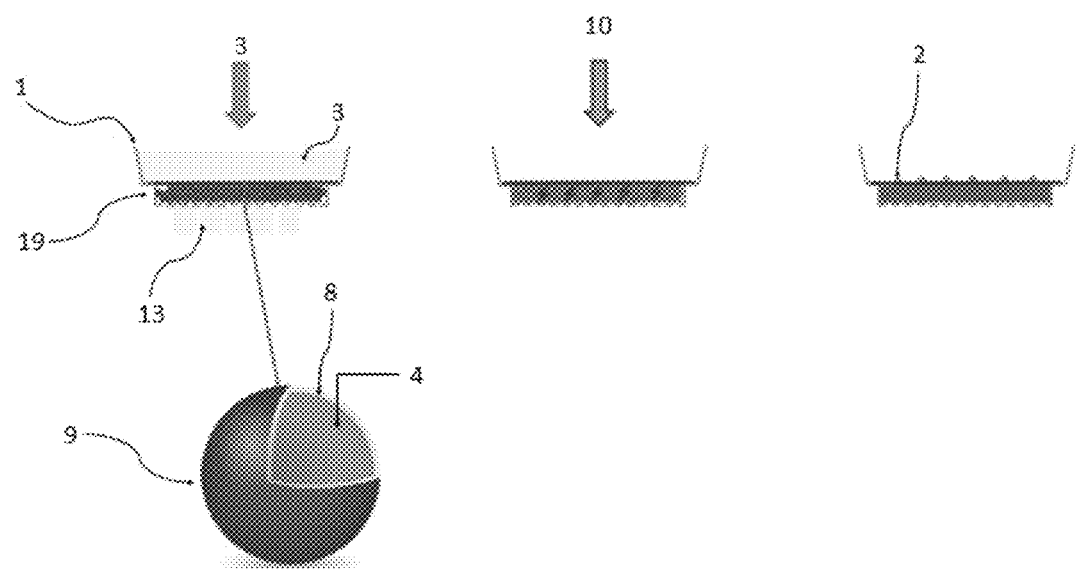
Figure 6:
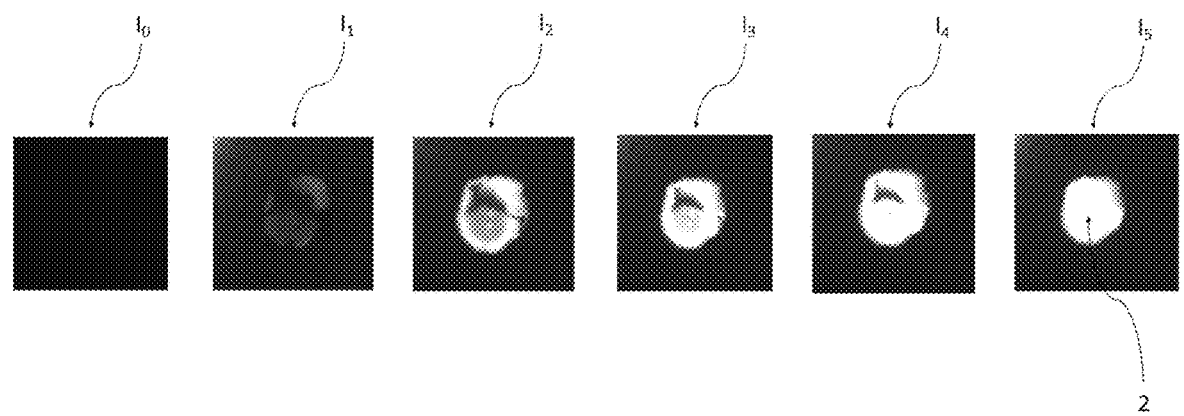
Figure 7:
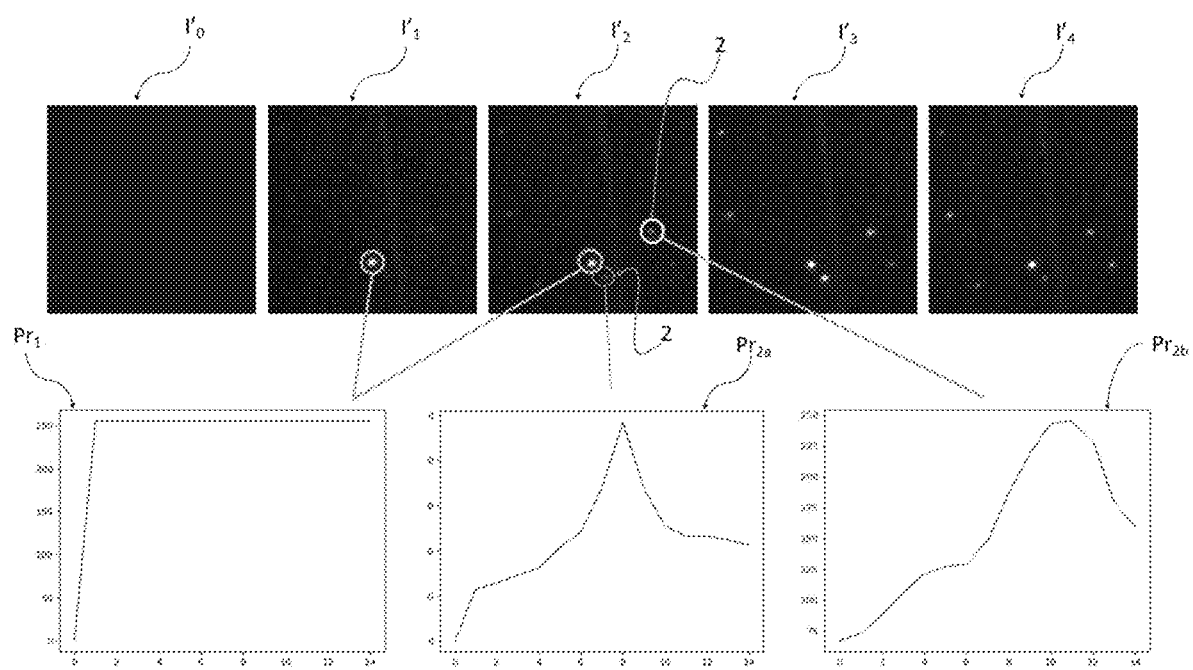

Other features and advantages of the invention will appear from the following detailed description of the non-limiting embodiments of the invention, which is given with reference to the accompanying figures, in which:

FIG. 1 diagrammatically shows the different steps of two specific embodiments of depositing a sample on a solid detection support, which steps can be implemented in the method for detecting at least one microorganism according to the invention;

FIG. 2 diagrammatically shows a specific method of implementing the various steps of the detection method of the invention, including in particular depositing a sample on a detection support, acquiring $P_0$ an image before staining said sample, then successively acquiring $P_1$ to $P_4$ a plurality of images after the controlled release of a cell marker, and carrying out a comparative analysis of the various images in order to produce an analysis result;

FIGS. 3A and 3B each diagrammatically show an exploded and perspective view, respectively in full and through a median section, of two non-limiting example embodiments of a detection support that can be used in the method or in the device of the invention;

FIGS. 4A and 4B each diagrammatically show an exploded and perspective view, respectively in full and through a median section, of an embodiment that differs from those shown in FIGS. 3A and 3B, and that is particularly preferred, of a detection support that can be used in the method or in the device of the invention;

FIG. 5 shows a specific embodiment of the detection method of the invention wherein the sample to be tested is brought into contact with an encapsulated cell marker, in the form of microcapsules, and which is released in a controlled manner under the action of an external stimulus to allow microorganisms potentially present in the sample to be detected;

FIG. 6 shows a series of acquisitions of images of *Bacillus subtilis* microcolonies, after a cultivation phase, the image on the left $I_0$ having been acquired before the release of a cell marker, whereas the other images $I_1$ to $I_5$ were acquired at regular intervals following the controlled release of said marker, allowing a staining kinetics of the *B. subtilis* colonies to be assessed via these successive image acquisitions;

FIG. 7 shows a series of five successive acquisitions of images, denoted by the references $I'_0$ to $I'_4$, of a detection support on which, on the one hand, dust is present and, on the other hand, cells to be detected in a test sample are present, in this case yeasts belonging to the *Candida* genus and the *albicans* species. Said support is photographed before the release of a cell marker (image $I'_0$) and after the controlled release of this marker (image $I'_1$ to $I'_4$) according to the method of the invention; said figure further shows three profiles $Pr_1$, $Pr_{2a}$ and $Pr_{2b}$ graphically showing, in parallel with the acquisitions of the images $I'_0$ to $I'_4$, a variation in light intensity (expressed in grey levels, representing the brightness of a pixel and encoded from 0 (black) to 255 (white)), after the staining, emitted by a dust capable of absorbing the cell marker ($Pr_1$) and by a yeast ($Pr_{2a}$ and $Pr_{2b}$) as a function of time, more particularly as a function of the successive image acquisitions, two consecutive image acquisitions being spaced 20 seconds apart, showing a sudden increase in the light intensity emitted by the dust after staining to an intensity that is strong and stationary over time, whereas the light intensity emitted by the yeasts gradually increases as the marker is assimilated by the cell, until it reaches a peak of maximum intensity before a decrease in light intensity, also known as photobleaching.

As shown in FIG. 1 to 7 of the accompanying drawings, the present invention firstly relates to a method for detecting, on a solid detection support 1, 21, at least one microorganism 2, or a plurality of microorganisms 2, potentially but not necessarily present in a sample 3 which is to be tested.

In the detection method of the invention, said one or more microorganisms 2, whether present in a unicellular form or in the form of microcolonies after a prior cultivation phase, are brought into contact with at least one cell marker 4.

The term "cell marker" is understood in the description hereinbelow to be a substance capable of revealing, by light emission, in particular by fluorescence, optionally by bioluminescence, or even by staining, the microorganisms potentially present in an original sample to be tested, it being understood that this cell marker can preferably be a fluorescent marker capable of revealing only viable microorganisms or of differentiating between viable and non-viable microorganisms, or even be capable of staining only certain pathogenic microorganisms of interest.

It should be noted that the sample 3 to be tested can originate, for example but in a non-limiting manner, from a pharmaceutical or food processing industry, or can consist of a sample of either human origin in clinical or medical microbiology, or of environmental origin, and the microorganisms 2 to be detected in said sample 3 are mainly of the bacteria, yeast or mould type.

In a first step a) of the detection method according to the invention, the sample 3 to be tested is deposited on said solid detection support 1, 21, preferably comprising at least one filtering membrane 5, 25.

In one example embodiment of step a) of the method of the invention, shown in the bottom part of FIG. 1, the sample 3 to be analysed consists of a liquid matrix, with a volume that can range from 1 mL to 500 mL, filtered through a detection support 1 comprising at least one filtering membrane 5, said support 1 being positioned on a device D suitable for the filtration.

Said membrane 5 has an adequate cut-off threshold to retain any microorganisms 2 potentially present in the sample 3 and to mainly remove, on the one hand, the residual liquid of said sample 3 and, optionally, on the other hand, the impurities contained therein, the size whereof is smaller than the cut-off threshold.

Thus, and regardless of the embodiment selected for implementing the first step a) of the method of the invention, said membrane 5, 25 preferably has a cut-off threshold comprised between 0.20 and 0.45 μm. Even more preferably, the cut-off threshold of this membrane 5, 25 is equal to, or in the order of, 0.30 μm.

Such a cut-off threshold makes it possible to retain, on the surface of said membrane 5, 25, all microorganisms 2 of the bacteria, yeast and mould type whose size varies between about 0.5 and about 10 μm, and which are liable to be present in the sample 3.

It should be noted, however, that the use of such a cut-off threshold not only promotes the separation of the microorganisms 2 from the rest of the sample 3, but also improves retention of most of the inert particles (such as dust) which are also originally present in said sample 3.

In a second example embodiment of step a) of the method of the invention, not shown in the figures, the liquid sample 3, with a volume comprised between 1 and 500 mL, is filtered through a filtering membrane 5 on a suitable filtration device D, said membrane 5 having a cut-off threshold comprised between 0.20 and 0.45 μm, and preferably equal to 0.3 μm.

Once the sample 3 has been filtered, the filtering membrane 5 is removed from the filtration device D to be deposited on the detection device 1.

Said detection support 1 can also be supplemented with at least one support disc 13 made of a permeable material, for example glass fibres.

Such a support disc 13 on which the filtering membrane 5 is optionally brought to rest after it has been removed from the device D to form, in this example embodiment, the solid detection support 1, is shown in particular in the accompanying FIGS. 3A and 3B.

In a third example embodiment, which is applied to a sample 3 of a smaller volume, typically between 10 and 2,000 μL, or less, said sample 3 is directly inoculated on the detection support 1, 21 comprising at least the membrane 5, 25 and the support disc 13, 23 as shown in the top part of FIG. 1.

Then, preferably, said detection support 1 is inserted into a fully automated detection device 14 capable of implementing the method of the invention. Said device 14 will be described in more detail hereafter.

It should be noted that, in one particularly advantageous example embodiment, step a) of depositing the sample 3 uses a detection support 21 configured to preferably allow for either the deposition of a small volume of the sample 3 comprised between 10 and 2,000 μL on a filtering membrane 25, or direct filtration of a larger volume of the sample 3 greater than 2,000 μL, typically up to a volume of 100 mL, without using a filtration device D dedicated to this operation and external to the detection device 14.

The sample 3 can be filtered in an automated manner in the detection device 14, even in the case of a small volume being deposited on the filtering membrane.

The detection support 21 will be described in detail in the description hereinbelow, with reference to FIGS. 4A and 4B.

It should be noted that, in a conventional manner, these operations of handling and depositing the sample 3 on the support 1, 21 can preferably be carried out by an operator in a sterile atmosphere, for example by carrying out said operations in a biological safety cabinet BSC, visible in FIG. 1.

In a step b) of the detection method according to the invention, shown in the accompanying FIG. 2, the detection support 1, 21 containing said sample 3 is illuminated at least once with light radiation 6 suitable for viewing or revealing said cell marker 4.

Indeed, in one specific example embodiment of the detection method of the invention, continuous illumination of the detection support 1, 21 throughout the implementation of said method is feasible. However, illuminating locally the detection support 1, 21, and simultaneously or almost simultaneously with each image acquisition, is even more preferable, as will be described in detail in the description hereinbelow.

After this illumination step b), and in a step c), at least one image $I_0$, $I'_0$ of the sample 3 is acquired on at least one portion of said detection support 1, 21, in a first phase $P_0$, two examples of the images $I_0$, $I'_0$ being visible in FIGS. 6 and 7.

The image acquisition taking place during the method of the invention is preferably carried out by means of an optical imaging device 7 having an optical resolution of more than or equal to 20 megapixels, preferably greater than 100 megapixels, enabling stained microorganisms having a size at least equal to 0.5 μm to be detected on a predetermined surface.

In a particularly important manner, said optical device 7 indeed has a relatively wide field of view, typically at least 10 mm long by at least 10 mm wide, and, even more preferably, this field of view is 25*25 mm, such that, for example, the entire detection support 1, 21 can be acquired in a single image.

It should also be noted that, preferably, said optical device 7 has a depth of focus of +/−0.5 mm in order to overcome any potential flatness defects of the membrane 5, 25 of said detection support 1, 21.

Thus, preferentially, in step c), a single image $I_0$, $I'_0$ of the entire surface of the detection support 1, 21 is acquired.

In the present method, when the size of the detection support 1, 21 is too large for it to be viewed by means of a single image acquisition, and in order to be able to observe a wider field without investing in a non-standard optical device creating economic conditions that are thus much less favourable, subjecting said detection support 1, 21 to n displacements along distinct paths can also be considered, where n is an integer greater than 1 and less than or equal to 20, and even more preferably less than or equal to 10.

By means of these n displacements along distinct paths, said detection support 1, 21 is spatially divided into n+1 portions, each of said portions being the subject of at least one image acquisition at the image acquisition times, in particular at $P_0$ and during at least one subsequent phase $P_i$ described in more detail hereinbelow, the sum of the image acquisitions of the different portions thus makes it possible to view the entire detection support 1, 21 at each of the different phases $P_0$, $P_i$.

Indeed, the ability to view the whole of said support 1, 21, whether in one go or more, is of particular interest to ensure a small number of germs is detected, or even a single germ initially present in the sample 3 to be tested.

Following the acquisition of the image $I_0$, $I'_0$ a step d) is carried out for the controlled release of at least one cell marker 4, through said detection support 1, 21, so that said marker 4 comes into contact with the microorganisms potentially present in the original sample 3 and deposited on the support 1, 21.

One specific embodiment of this controlled release step d) is more particularly shown in FIG. 5.

Preferably, the cell marker 4 implemented in the method of the invention is a fluorescent marker.

This marker 4 can be advantageously selected by a person skilled in the art from among all cell markers well known thereto and commonly used, for example, in current cytometry techniques.

Thus, said cell marker can be selected, for example, from the following markers: DNA markers such as acridine orange, DAPI (4',6-diamidino-2-phenylindole), PI (propidium iodide), DRAQ7* (Deep Red Anthraquinone 7), 7-AAD (7-aminoactinomycin D), TO-PRO-1*, TO-PRO-3*, SYTOX*, LDS 751, ethidium bromide, eosin-5'-maleimide (EMA), amine-reactive markers such as "Zombie Fixable*", "Fixable Viability Dye eFluor*", "LIVE/DEAD Fixable dead*", "Viobility Fixable*", "Horizon Fixable Viability*", "Ghost*", esterase activity markers such as calcein AM (acetoxymethyl), cFDA (Carboxyfluorescein diacetate), "CellTracker Green CMFDA*", redox markers such as resazurin or tetrazolium salts, or cell markers in kits such as the "LIVE/DEAD Viability*" kits, the names of the reagents mentioned in this paragraph and followed by an asterisk being registered trademarks.

A combination of a plurality of cell markers from those mentioned hereinabove can also be used.

It should be noted that, in the case whereby a fluorescent cell marker 4 is used in the method of the invention, the light radiation 6 is selected from a laser beam and one or more light-emitting diodes, the latter solution being particularly preferred.

In an alternative embodiment of the present method, in step d), the one or more potential microorganisms 2 present can also be brought into contact with at least one non-fluorescent but visible and detectable cell marker 4.

Said cell marker 4 can further consist of a bioluminescent marker, it being understood that in this scenario, the method for detecting microorganisms of the invention is implemented by removing the one or more steps of illuminating the detection support 1, 21. In other words, with the exception of the illumination of the support, all the other steps, alternative embodiments and example embodiments of the method of the invention described in detail in the present description are applicable to a method for detecting microorganisms by bioluminescence, if this proves to be adapted and feasible, implementing, of course, a suitable bioluminescent marker.

In any case, in a particularly advantageous manner, in a first precise and non-limiting embodiment of step d) of controlled release, the cell marker 4 that is to be released in a controlled manner during the method of the invention is encapsulated in an encapsulation means 8 thus advantageously forming a microcapsule, a microbead or a microsphere 9, having a diameter that is, for example, in the order of 100 μm.

Preferably, the encapsulation means 8 is sensitive to the application of an external stimulus 10 causing it to rupture and release the cell marker 4.

Thus, preferably, the encapsulation means 8 is formed by heat-sensitive lipid waxes and the release of the encapsulated marker 4 is obtained by gradually applying a temperature rise to said encapsulation means 8 such that the latter melts and releases the marker 4 in contact with potential microorganisms 2 to be detected.

In such a case, the temperature to which said heat-sensitive encapsulation means 8 is subjected can be gradually raised from an ambient temperature to a temperature not exceeding 45° C., above which threshold certain microorganisms 2 could be destroyed.

In the invention, the release of the cell marker 4 is preferably carried out in an automated manner, thus freeing it from any manual operation constituting a source of contamination, and is controlled so as to occur with the adequate quantity of marker 4 and at the right kinetics for efficiently staining the microorganisms 2.

According to a first alternative embodiment, the cell marker 4 is encapsulated in liquid form, the microcapsule 9 thus including, in addition to said marker 4, a solvent for the dissolution thereof.

In a second alternative embodiment, the cell marker 4 is encapsulated in solid form, in particular in the form of a powder. Following the release of the cell marker 4, the latter is then placed in the presence of a suitable dissolving solvent, for example water, so that the staining of the microorganisms 2 can take place.

Preferably, in this alternative embodiment, the solvent for dissolving the solid cell marker 4 is contained in the glass fibre support disc 13 and the filtering membrane 5 through which the sample 3 was passed is disposed above said support disc 13.

Thus, once the filtering membrane 5 has been deposited above the support disc 13 (after external filtration of the sample 3), or once the sample 3 has been deposited and filtered directly on the filtering membrane 5 in the detection support 1, regardless of the volume of the sample 3, a layer of microcapsules 9 containing the cell marker 4 being positioned between said membrane 5 and said disc 13, said support disc 13 is soaked with an adequate solvent to allow, once the cell marker 4 has been released from the capsule 9 thereof (for example by increasing the temperature), the latter to be dissolved. This example is shown in FIG. 3B.

In the configuration shown in FIG. 3B, the support disc 13 can also be soaked with a suitable solvent and kept at a temperature that is capable of melting the encapsulation layer 8, thus releasing the encapsulated cell marker 4 in solid powder form while simultaneously dissolving it to reveal the potential presence of microorganisms 2 on the membrane 5.

In any case, when a layer of microcapsules 9 containing the cell marker 4 in solid or liquid form is positioned above the support disc 13, the main function thereof, after rupture of said microcapsules 9, is to homogenise, by diffusion, the distribution of said marker 4 beneath the membrane 5, which is itself placed above the layer of microcapsules 9. Thus, each microorganism 2 liable to be present at said membrane 5 will be revealed by the method of the invention.

It should also be noted that, in this embodiment of step d) and when step a) of depositing the sample 3 having a small volume (10 to 2,000 μL) is carried out directly on the solid detection support 1, which, again, can be formed by at least one support disc 13 and a filtering membrane 5 surrounding a layer of microcapsules 9, said support disc 13 further fulfils a function of supporting said microcapsules 9 to prevent them from being discharged with the filtered liquid during the deposition.

In FIG. 3A, the layer of microcapsules 9 is placed beneath the support disc 13, which is for example made of glass fibres, and said disc 13 ensures the capillary diffusion of said microcapsules 9 or of the cell marker 4 once the latter has been released in a controlled manner, as well as a homogeneous distribution of these microcapsules 9 diffused beneath the filtering membrane 5.

A controlled release of a cell marker 4 by destroying the encapsulation means 8 in which said marker 4 is contained, although proving to be of particular interest, must not be considered to be the sole embodiment of step d) of the method of the invention.

Indeed, in a second embodiment of this step d), the cell marker 4 is conveyed directly in the form of a liquid solution, and in a controlled and automated manner, for example at a flow rate controlled by appropriate means, such as a controlled-flow pump, in order to be brought into contact with the one or more microorganisms 2 present at the surface of the filtering membrane 5, 25 of the detection support 1, 21.

In this case, regardless of the mode of release chosen for bringing the cell marker 4 into contact with the one or more microorganisms 2 in a controlled manner, said marker 4, whether it is preferably fluorescent, or instead bioluminescent or otherwise, preferably has minimal toxicity with respect to the microorganisms 2 potentially present on the membrane 5.

Indeed, in the event that contamination of the sample 3 is detected during the implementation of this method, and in certain applications, in particular in the industrial pharmacy field, the ability to subsequently identify the microorganism 2 detected can be of particular interest.

Such an identification step 12, shown in FIG. 2, can thus be carried out by cultivating the sample 3 after detection, in particular by removing the filtering membrane 5, 25 and depositing it on a suitable nutrient agar allowing the microorganisms to multiply, then by implementing a conventional identification method well known to a person skilled in the art, for example by mass spectrometry.

In the method for detecting one or more microorganisms according to the invention, at the end of the step of the controlled release of at least one cell marker 4, at least one image $I_i$, where i is an integer greater than or equal to 1, is acquired, in a step e), and during at least one phase $P_i$ subsequent to the phase $P_0$.

FIGS. 6 and 7 show a succession of images, $I_0$ to $I_5$ and $I'_0$ to $I'_4$ respectively, acquired during the phase $P_0$ and during a plurality of subsequent phases after $P_0$.

Each image $I_i$ acquired during at least one subsequent phase $P_i$ is, where appropriate, cut into portions of said detection support 1, 21.

Such a succession of acquisitions of images, one (for example $I_0$) being acquired before the staining of microorganisms 2 by the controlled release of the cell marker 4 and at least one other ($I_i$) after this release, makes it possible to characterise a staining kinetics of these microorganisms 2, in other words a change in the behaviour, and in particular, preferably, in the fluorescence, optionally in the bioluminescence, of said microorganisms, corresponding to an assimilation of the marker 4 thereby, between the first acquisition of an image $I_0$ without the marker 4 and at least the second acquisition of an image $I_i$ after the release thereof.

This makes it possible to differentiate the behaviour of inert particles, for example dust, liable to emit, for example, a natural fluorescence, from the microorganisms 2 effectively stained during the implementation of the method.

Indeed, in this hypothesis where the potential microorganisms 2 are revealed by means of a fluorescent cell marker 4, the inert particles or dust naturally fluorescent and which have been retained on the filtering membrane 5 will be visible and detectable in the image $I_0$ before the controlled release of said marker 4 and in at least one image $I_i$ after this release, whereas said microorganisms 2 will only be visible and detectable in the image $I_i$, in particular in the image $I_1$ or $I'_1$.

The subsequent step f), during which a comparative analysis of said images $I_0$ and $I_i$, in particular of at least $I_1$ or $I'_1$, is carried out, will allow a conclusion to be drawn as regards the presence or absence of microorganisms 2 in the original sample 3.

Considering the hypothesis that, during the phase $P_0$, said detection support 1, 21 was subjected to n displacements along distinct paths, this support 1, 21 is again subjected, during the phase $P_i$, to n identical displacements such that the images $I_0$ and $I_i$ acquired respectively at $P_0$ and $P_i$ can be compared in a subsequent comparative analysis step (step f)).

Moreover, a similar logic is applied to the subsequent images, where present.

Indeed, in one preferred embodiment, shown in FIGS. 6 and 7, after a first acquisition of an image $I_1$, $I'_1$ during a first subsequent phase $P_1$, after a variable lapse of time, in the order of a few seconds to a few tens of seconds, for example between 10 and 30 seconds, an image $I_2$, $I'_2$ is again acquired of each portion of said support 1 of which an image was acquired during the phases $P_0$ and $P_1$.

Thus, in the detection method of the invention, the step e) of acquiring an image $I_i$, can feasibly and advantageously be repeated several times after step d) of the controlled release of the cell marker 4 and before step f) of the comparative analysis of the images $I_0$, $I'_0$; $I_1$, $I'_1$; $I_2$, $I'_2$, etc., the successive acquisitions of the images $I_i$ being spaced apart by a lapse of time comprised between 10 and 30 seconds, preferably equal to 20 seconds.

It goes without saying that each image is stored in memory by the device 14 for subsequent processing operations, in particular for comparison.

Preferably, step e) of the present method is repeated three times in succession before the comparative analysis step f), so as to generate three images $I_1$, $I'_1$; $I_2$, $I'_2$; $I_3$, $I'_3$, of each portion of the detection support 1, 21 of which an image was acquired at $P_0$ during subsequent image acquisition phases $P_1$, $P_2$ and $P_3$ respectively.

Even more preferably, five images from $I_1$ to $I_5$ or from $I'_1$ to $I'_5$ (image $I'_5$ not being shown in FIG. 7, however) are generated of each of the portions of the detection support 1, 21 having been viewed during the phase $P_0$.

Thus, by releasing, in a particularly original manner, the cell marker 4 after depositing the sample 3 on the detection support 1, 21 and also after a first acquisition of an image $I_0$ in the phase $P_0$, the microorganisms 2 hypothetically present in said sample 3 will be stained, preferably as early as the unicellular marker stage, in a short lapse of time, in the order of a few minutes, corresponding to the kinetics of the assimilation reactions of the cell marker 4 by the microorganism 2, thus procuring a rapid detection result by successively acquiring images $I_0$, $I'_0$; $I_1$, $I'_1$, etc., of the support 1, 21 after staining during the various phases $P_0$, $P_1$, etc.

Depending on the nature of the cell marker 4 used in step d) of the method, the biochemical reaction of the assimilation thereof by a microorganism 2 can be, in particular, either an enzymatic reaction, or an oxidation-reduction reaction, or even a reaction intercalating said marker between the bases of a nucleic acid.

The characterisation of a staining kinetics of the microorganisms 2 potentially present in the sample 3 to be tested also makes it possible to quickly differentiate the behaviour of inert particles or dust, liable to naturally emit fluorescence, from that of said microorganisms 2, leading to a significant reduction in false positives compared to the systems proposed in the prior art.

It is also clear from the above that the implementation of the method of the invention allows for the detection of a single contaminant corresponding to a CFU, i.e. a Colony-Forming Unit, according to the terminology used by a person skilled in the art, which could be contained in the original sample 3.

The conclusion as to whether or not said sample 3 is contaminated is drawn at the end of step f) of carrying out a comparative analysis between the image $I_0$; $I'_0$ acquired during the first phase $P_0$, and at least the image $I_i$ (for example the image $I_1$; $I'_1$), already mentioned hereinabove in the description and which is advantageously implemented by means of an image detection and processing algorithm 11.

It should also be noted that, when the presence of at least one contaminating microorganism 2 is detected during this analysis step f), a step g) of enumerating the one or more microorganisms 2 present in the sample 3 and on the detection support 1, 21 can be carried out.

This optional step g) can also be carried out by the algorithm 11.

This algorithm 11 must thus allow, in particular, the presence or absence of microorganisms 2 in the images $I_1$, $I'_1$, $I_2$, $I'_2$, etc., to be quickly detected as accurately as possible, by assessing the change in the behaviour of said microorganisms 2 over time, and by distinguishing them from any potential artefacts, in particular from dust, and then must allow these microorganisms 2 to be enumerated.

Moreover, the algorithm 11 is preferably capable of detecting elements (dust, microorganisms, etc.), having dimensions in the order of, or less than, the resolution of the sensors of the optical imaging device 7.

This is one of the primary advantages of the invention: the use of a method based on the kinetics of the assimilation of the cell marker 4 by the microorganisms 2 overcomes, to a certain extent, the optical resolution requirements.

Indeed, the fluorescence intensity variation resulting from the staining kinetics can be detected on a single pixel. The size of the microorganism 2 is thus not necessarily greater than the size of a pixel. In some cases, the light intensity emitted by a microorganism 2 that is smaller than a pixel is just enough to illuminate said pixel. Although this intensity can be insufficient for detecting the microorganism 2 with certainty, the variation in intensity during the staining can be sufficient for the detection thereof.

Preferably, step e) of acquiring an image $I_i$ of the detection support 1, 21 after the controlled release of the cell marker 4, is carried out with a time delay following the release of said marker 4 typically comprised between 20 and 300 seconds, preferably between 80 and 160 seconds in the case of staining with acridine orange for example.

Such a time delay after the controlled release of the marker 4, and thus after said marker 4 is brought into contact with a microorganism 2 potentially present on the detection support, respectively before the image $I_i$ is acquired, makes it possible to ensure that said microorganism 2 has correctly assimilated said marker 4.

In one highly preferred example embodiment, the detection support 1, 21 is illuminated locally by light radiation 6 capable of revealing the cell marker 4, simultaneously, or almost simultaneously, with each of the image acquisitions carried out, both the initial acquisition of an image $I_0$, $I'_0$ of step b) in a first phase $P_0$, and simultaneously with the acquisition of an image I which takes place in at least one subsequent phase $P_i$.

In other words, outside of the image acquisition phases $P_0$ and $P_i$, the detection support 1, 21 can be not illuminated by the light radiation 6.

It should be noted that, preferably, the method of the invention includes at least the following steps, in this order:
- a1) Depositing the sample 3 to be analysed on said solid detection support 1, 21;
- b1) Illuminating said detection support 1, 21 locally by light radiation 6 capable of revealing said at least one cell marker 4;
- c1) Simultaneously with the illumination step b1), acquiring at least one image $I_0$, $I'_0$ in a first phase $P_0$ of said sample 3 on at least one portion of said detection support 1, 21 by means of an optical imaging device 7 having a resolution at least equal to 20 megapixels and a field of view that is at least 10 mm long by at least 10 mm wide;
- d1) Carrying out a controlled release of the cell marker 4, or of a succession of cell markers 4 or reagents, through the detection support 1, 21, to bring said marker 4 into contact with said microorganism 2;
- e1) Within a lapse of time of less than 5 seconds after step d1) of the controlled release of said cell marker 4, illuminating said detection support 1, 21 locally with said light radiation 6 capable of revealing said at least one cell marker 4;
- f1) Simultaneously with the illumination step e1), acquiring an image $I_1$, $I'_1$ of each portion of the detection support 1, 21 of which an image $I_0$, $I'_0$ was acquired at $P_0$ in at least one subsequent phase $P_1$ after the step of the controlled release of said marker 4;
- g1) Re-illuminating, at least once, said detection support 1, 21 locally with said light radiation 6;
- h1) Simultaneously with the illumination step g1), acquiring an image $I_2$, $I'_2$ of each portion of the detection support 1, 21 of which an image $I_0$, $I'_0$ was acquired at $P_0$ and an image $I_1$, $I'_1$ was acquired at $P_1$ in at least one second subsequent phase $P_2$ in order to detect said at least one microorganism 2 according to the change in the staining kinetics of said microorganism 2;
- i1) Carrying out a comparative analysis, per portion of the detection support 1, 21, between said image $I_0$, $I'_0$ acquired at $P_0$ and said images $I_1$, $I'_1$; $I_2$, $I'_2$ acquired in at least two subsequent phases $P_1$ and $P_2$ and drawing a conclusion as regards the presence or absence of at least one microorganism 2 in said sample 3.

Steps g1) and h1) for acquiring the image $I_2$, $I'_2$ are preferably implemented in a lapse of time of 20 and 300 seconds, preferably between 80 and 160 seconds, after step f1) in which the image $I_1$, $I'_1$ is acquired.

It should be noted that the alternative embodiments or preferred examples of steps a) to f) described hereinabove in the description are also applicable to the corresponding steps a1) to i1) of the method presented in the paragraph hereinabove.

Such a method is of particular interest since it allows, on the one hand, effective discrimination between:
- A first category of inert particles or dust that naturally emit, for example, fluorescence or bioluminescence, and that will be viewed in the image $I_0$, $I'_0$ acquired in a first phase $P_0$, before step d1) of the controlled release of the cell marker 4;
- A second category of inert particles or dust, that are not autofluorescent (and thus not visible in the image $I_0$, $I'_0$) but that rapidly absorb the cell marker 4 after the controlled release thereof, this dust thus being clearly visible in the image $I_1$, $I'_1$;
- The one or more microorganisms 2 potentially present in the original sample 3 to be analysed, and which will not be visible in the image $I_0$, $I'_0$, can start to appear in the image $I_1$, $I'_1$, with a low light intensity, and which are then clearly visible, with a higher light intensity, in the images $I_2$, $I'_2$ and potential subsequent images, it being understood that steps g1) and h1) can be repeated as many times as desired to acquire images during subsequent phases $P_2$, $P_3$, etc.

FIG. 7 shows a series of acquisitions of images I'$_0$ to I'$_4$, and matches some of the elements visible in these images, in particular in the images I'$_1$ to I'$_4$, with the profiles Pr$_1$, Pr$_{2a}$ and Pr$_{2b}$, showing the variation in light intensity of the elements in question as a function of time after the moment (0 on the abscissa) when the cell marker 4 is released in a controlled manner and brought into contact with said elements, in this case dust and *Candida albicans* yeasts present in the sample 3 and on the solid detection support 1, 21.

In the image I'$_0$, acquired before the step of the controlled release of the cell marker 4, no elements are visible. This image I'$_0$ thus shows that that there is no dust naturally emitting light in said original sample 3.

In the following images I'$_1$ to I'$_4$, after staining, some elements present in said sample 3 can be seen to have a light intensity that is strong and substantially constant over time, after the staining step. In this case, the comparison between the successive images I'$_1$ to I'$_4$ leads to the conclusion that this is dust that has absorbed the cell marker and the profile Pr$_1$ whereof is shown graphically in connection to the identified spot of light.

In the succession of images I'$_1$ to I'$_4$ after staining, other elements are also seen, in this case microorganisms, the light intensity whereof, shown on the profiles Pr$_{2a}$ and Pr$_{2b}$, gradually increases over time until reaching an intensity peak, corresponding to a gradual assimilation of the cell marker 4 by a microorganism 2 (*Candida albicans* yeasts in this case), before this light intensity decreases, also in a gradual manner, which corresponds to the photobleaching phenomenon.

It should be noted that, in the event that an inert particle, for example dust, which naturally emits light, had been deposited on the detection support 1, 21 in the first step a1) of the method of the invention, this would have been visible in the image I'$_0$ and in all of the subsequent images I'$_i$. Such dust could thus also have been differentiated from a microorganism 2 by implementing the detection method according to the present invention.

The present invention further relates to a device 14 for automatically detecting at least one microorganism 2, of the bacteria, yeast or mould type, potentially present in a sample 3 to be tested, and capable of implementing the steps of the detection method described hereinabove.

Advantageously, the device 14 according to the invention includes at least:
- a solid detection support 1, 21 intended to receive said sample to be analysed 3 which is liable to contain at least one microorganism 2. This support 1, 21 preferably consists of at least one filtering membrane 5, 25, through which the sample 3 is passed, and of a support disc 13, 23 on which the membrane 5, 25 rests.

In the embodiment shown in FIGS. 3A and 3B, the detection support 1 can be supplemented by a protective cover 16 and by a means for holding all of the elements of the support 1 on a rigid support plate 18, said holding means being capable of taking the form of a hoop 17.

In another embodiment, shown more specifically in FIGS. 4A and 4B, the detection support 21, comprising a filtering membrane 25 resting on a glass fibre support disc 23, is supplemented by:
- a support means 24 which is rigid and in particular made of plastics material, and which is permeable, through the presence of a plurality of circular perforations and/or oblong perforations, said rigid support means 24 being also referred to, in the description hereinbelow, as a drain 24; the latter has a shape and dimensions that are similar or somewhat similar to those of the support disc 23 and of the filtering membrane 25;
- a rigid base 26, made for example of plastics material, through which passes, on the one hand, a feed line 26a feeding a liquid, in this case the cell marker 4, said line 26a being extended by a vent 26b projecting from said base 26 and passing through a first orifice 24a made in the drain 24 and a second orifice 23a made in the support disc 23, for example made of glass fibres, and, on the other hand, an aspiration and discharge line 26c for a liquid; this line 26c is connected, by appropriate means, to a recipient for receiving the residual liquid discharged with a view to the subsequent treatment or the destruction thereof;
- a clamping ring 27 holding all of the components of the detection support 21 together such that they are integral with one another; for this purpose, the clamping ring 27 and the base 26 preferably have a thread and said clamping ring 27 is capable of clamping all of the components of the detection support 21;
- a gasket 28 that can be added to guarantee the leakproof sealing of the detection support 21.
- a means of storing at least one cell marker 4 of said microorganism 2.

In one embodiment, shown in FIGS. 3A and 3B, the storage means 19 is included in the detection support 1. More specifically, such a storage means 19 is preferentially positioned beneath the filtering membrane 5, and preferably between said membrane 5 and the glass fibre support disc 13. Such a storage means 19 is also shown in FIG. 5 and advantageously takes the form of a layer of microcapsules 9, each microcapsule 9 in the layer being formed by the cell marker 4 encapsulated in an encapsulation means 8. This storage means 19 could also feasibly be positioned beneath the glass fibre support disc 13, on which the filtering membrane 5 thus directly rests.

In another embodiment, wherein the detection device 14 includes the detection support 21 shown in FIGS. 4A and 4B, the means for storing the cell marker 4 consists of a reserve of liquid solution of the marker 4, this reserve being separate from said detection support 21 and said device 14 thus comprising means for conveying the cell marker 4 from said storage means to said detection support 21. These means of conveying the cell marker 4 in liquid form are thus connected, by appropriate connecting means, to the liquid feed line 26a of the base 26 of the detection support 21. Via the feed line 26a, then via the vent 26b of the base 26 which passes through the drain 24 via the orifice 24a and the support disc 23 via the orifice 23a, the cell marker 4 in liquid form will, in this scenario, be conveyed directly to the top of said support disc 23, beneath the filtering membrane 25 liable to contain the microorganisms 2 to be detected.

- a means 15 for the controlled release of said cell marker 4 for bringing said marker 4 into contact with said sample 3 to be analysed.

Such a means can include, for example, in the embodiment whereby the means for storing at least one cell marker 4 takes the form of a layer of microcapsules 9, means of heating the detection support 1, associated with conventional means of controlling and regulating the temperature, in order to apply a temperature rise to melt the encapsulation means 8 and release the marker 4.

In another example embodiment, the cell marker 4, preferably in liquid form, can be gradually conveyed at the appropriate time from a separate reserve to the detection support 1, 21 from beneath it, in particular beneath the support disc 13, 23 and be diffused by capillarity by means of this disc 13, 23 in order to bring the marker 4 into contact with the microorganisms 2 capable of being retained on the membrane 5, 25. In such a case, the means 15 of controlled release, shown very diagrammatically in the form of an injection syringe in FIG. 2, can consist of means for aspirating the liquid marker 4 and means for regulating the feed flow rate, for example a flow-controlled pump;

- a means 6 of illuminating said detection support 1, 21 capable of revealing the cell marker 4, in particular based on a laser beam or, even more preferably, high-power light-emitting diodes;
- an optical device 7 for acquiring images of at least one portion of said detection support 1, 21 and positioned above this support 1, 21, said optical device 7 preferably having a resolution that is at least equal to 20 megapixels, more preferably at least equal to 100 megapixels. This optical device 7 more preferably has a depth of focus in the order of 0.5 mm, or equal to 0.5 mm to overcome defects concerning the flatness of the detection support 1 to be viewed. It advantageously consists of a camera with CMOS sensors and has a field of view, the dimensions whereof are, for example, at least 10 mm long by at least 10 mm wide, and even more preferably, 25*25 mm.

The detection support 1, 21 can furthermore cooperate with means for displacing said detection support 1, 21 beneath this optical imaging device 7, in the event that the detection support 1, 21 must be divided into a plurality of portions for acquiring images before and after staining and for observing a wider field. These displacement means are not shown in the figures.

- means for storing in memory, for comparing and for analysing the images acquired by the optical device 7 so as to detect said at least one microorganism 2 potentially present in said sample 3 according to the change in the staining kinetics of said at least one microorganism 2. Such means of analysis preferably consist of an image detection and processing algorithm 11.

FIGS. 4A and 4B show a particularly preferred embodiment of a solid detection support 21, intended to receive said sample to be analysed 3 liable to contain at least one microorganism 2, and which can be implemented in the detection method according to the invention or be part of the detection device 14 capable of implementing the steps of this method.

As shown in FIGS. 4A and 4B, this detection support 21 consists of at least one filtering membrane 25, through which the sample 3 is passed, and of a glass fibre support disc 23 on which the membrane 25 rests.

Such a detection device is also provided with a rigid support means 24, or drain 24 that is permeable through a plurality of circular perforations and/or oblong perforations. The glass fibre support disc 23, positioned underneath said filtering membrane 25, rests on this drain 24. Thus, these three elements, the support disc 23, the drain 24 and the filtering membrane 25 advantageously have a shape that is essentially circular, as well as similar or somewhat similar dimensions.

Such a rigid and permeable support 24 maintains, in particular, the flatness of the flexible elements supported thereby, the disc 23 and the membrane 25, which are capable of becoming deformed when implementing the method of the invention, or by the deposition of the sample 3 on the surface of said membrane 25, by the aspiration of the residual liquid, etc. Furthermore, due to the presence of numerous perforations, liquid can be discharged through this support 24.

Said rigid support or drain 24 is itself mounted on a rigid base 26 through which at least one liquid feed line 26a passes and through which at least one liquid aspiration and discharge line 26c passes.

The purpose of said feed line 26a is to convey the liquid cell marker 4 to the detection support 21, said line 26a being moreover extended by a vent 26b projecting from said base 26 and passing through, on the one hand, a first orifice 24a made in the drain 24 and, on the other hand, a second orifice 23a made in the glass fibre support disc 23 so as to bring the liquid cell marker 4 into immediate contact with the filtering membrane 25 and thus with the microorganisms 2 potentially contained therein.

In addition to the feed line 26a, at least one aspiration and discharge line 26c also passes through the base 26 for a liquid, whether this is excess liquid cell marker 4 after being brought into contact with the filtering membrane 25, or any other liquid, for example the residual liquid of the sample 3 after filtration by the membrane 25, or a washing liquid.

A clamping ring 27, which holds all of the components of the detection support 21 together such that they are integral with one another, and optionally a gasket 28 supplement said support 21.

It should be noted that, regardless of the embodiment selected as regards the detection support 1, 21, the filtering membrane 5, 25 is advantageously dark in colour, preferably black in colour, in order to allow for optimal revelation of the fluorescence or of the bioluminescence of the cell marker 4, by contrast between the light emitted and the dark shade of said filtering membrane 5, 25.

If the detection method or the detection device 14 of the invention is implemented for the purpose of detecting cells or microorganisms 2 in the unicellular stage, a membrane 5, 25 made of polyester or polycarbonate will be preferred, whereas, to detect clusters of cells in the form of microcolonies, after a cultivation phase, a membrane 5, 25 made of cellulose nitrate or ester will be preferred.

Generally speaking, the elements described hereinabove for the detection method can be applied to the detection device and to the detection supports 1, 21 according to the invention, and vice-versa, if this proves to be appropriate and feasible.

It goes without saying that the invention is not limited to the examples shown and described hereinabove, which can be subjected to alternatives and modifications while still remaining within the scope of the invention.

The invention claimed is:

1. A method for detecting, on a solid detection support, at least one microorganism, of bacteria, yeast or mould type, present in a sample to be analysed and revealed by means of at least one cell marker, said method comprising at least the steps, in a sequential order, of:
   a1) depositing said sample to be analysed on said solid detection support;
   b1) illuminating locally said detection support by light radiation capable of revealing said at least one cell marker;
   c1) simultaneously with the illumination step b1), acquiring at least one image ($I_0$, $I'_0$) in a first phase $P_0$ of said sample on at least one portion of said detection support by means of an optical imaging device targeting a field of view that is at least 10 mm long by at least 10 mm wide;

d1) carrying out a controlled release of said at least one cell marker, through the detection support, to bring said marker into contact with said microorganism;

e1) within a lapse of time of less than 5 seconds after step d1) of the controlled release of said cell marker, illuminating locally said detection support with said light radiation capable of revealing said at least one cell marker;

f1) simultaneously with the illumination step e1), acquiring an image ($I_1$, $I'_1$), by means of said optical device, of each portion of the detection support of which an image was acquired at $P_0$ in at least one subsequent phase $P_1$ after the step of the controlled release of said marker;

g1) re-illuminating locally, at least once, said detection support with said light radiation;

h1) simultaneously with the illumination step g1), acquiring an image ($I_2$, $I'_2$), by means of said optical device, of each portion of the detection support of which an image was acquired at $P_0$ and at $P_1$ in at least one second subsequent phase $P_2$ in order to detect said at least one microorganism according to the change in the staining kinetics of said microorganism; and i1) carrying out a comparative analysis, per portion of the detection support, between said image ($I_0$, $I_0$) acquired at $P_0$ and said images ($I_i$, $I'_1$; $I_2$, $I'_2$) acquired in at least two subsequent phases $P_1$ and $P_2$ and drawing a conclusion as regards the presence or absence of at least one microorganism in said sample.

2. The detection method according to claim 1, wherein said detection support is illuminated locally, with light radiation every time an image is acquired at $P_0$, $P_i$.

3. The detection method according to claim 1, wherein the detection support is subjected to n displacements along distinct paths with a view to spatially dividing said detection support into n+1 portions, images whereof are acquired in at least two phases $P_0$ and $P_i$, where n is an integer less than or equal to 20.

4. The detection method according to claim 1, wherein an optical imaging device having a resolution at least equal to 20 megapixels is used in the image acquisition steps c1), f1) and h1).

5. The detection method according to claim 1, further comprising the step of in response to a conclusion that at least one microorganism is present in said sample in step i1), carrying out an enumeration of the microorganisms present in said sample.

6. The detection method according to claim 1, wherein said cell marker is a fluorescent marker.

7. The detection method according to claim 1, wherein said cell marker released in a controlled manner in step d1) is encapsulated in an encapsulation means.

8. The detection method according to claim 7, wherein said cell marker is encapsulated in an encapsulation means in solid form, for example in the form of a powder, and wherein said detection support comprises a solvent for dissolving said marker.

9. The detection method according to claim 7, wherein said cell marker is encapsulated in liquid form.

10. The detection method according to claim 7, wherein said encapsulation means is heat-sensitive and, in step d1), a controlled release of the cell marker encapsulated in said heat-sensitive encapsulation means is carried out by subjecting the latter to a temperature rise capable of melting said heat-sensitive encapsulation means.

11. The detection method according to claim 10, wherein the temperature is raised from ambient temperature to a maximum temperature of 45° C.

12. The detection method according to claim 1, wherein the cell marker in a liquid solution is conveyed, in a controlled manner, to said solid detection support containing the sample to be analysed.

13. The detection method according to claim 1, wherein a volume comprised between 10 and 2,000 µL of said sample to be analysed is deposited directly on said detection support.

14. The detection method according to claim 1, wherein said sample to be analysed is filtered through a filtering membrane having a cut-off threshold comprised between 0.2 and 0.45 µm, said filtering membrane being positioned directly in said detection support.

15. The detection method according to claim 1, wherein in order to distinguish microorganisms from dust on the detection supports having received the samples to be analysed, the following steps are implemented:
measuring, after each image acquisition, the brightness of the luminescent pixels or clusters of pixels detected;
comparing the brightness of each luminescent pixel or cluster of pixels detected in the different images;
identifying the pixels or clusters of pixels having a brightness that does not substantially change in at least two consecutive images during the staining kinetics; and
analysing and counting the pixels or clusters of pixels having a brightness that changes during the staining kinetics.

16. A device for detecting at least one microorganism, of the bacteria, yeast or mould type, present in a sample to be analysed, and capable of implementing the method of claim 1, said device comprising at least:
a solid detection support intended to receive said sample to be analysed which is liable to contain at least one microorganism;
a means of storing at least one cell marker of said microorganism;
a means for the controlled release of said cell marker for bringing said marker into contact with said sample to be analysed;
a means of illuminating said detection support;
an optical device for acquiring images of at least one portion of said detection support, said optical device having a field of view that is at least 10 mm long by at least 10 mm wide; and
means for storing in memory, for comparing and for analysing the images acquired by the optical device so as to detect said at least one microorganism potentially present in said sample according to the change in the staining kinetics of said at least one microorganism.

17. The detection device according to claim 16, further comprising means for displacing said detection support beneath said optical imaging device.

18. The detection device according to claim 16, wherein said solid detection support includes at least one filtering membrane resting on a glass fibre support disc.

19. The detection device according to claim 18, wherein said means for storing the cell marker is included in the detection support and consists of a layer of microcapsules formed by said cell marker encapsulated in an encapsulation means, said layer of microcapsules being disposed between said glass fibre support disc and said filtering membrane.

20. The detection device according to claim 19, wherein said means for the controlled release of the cell marker includes heating means and temperature control and regulation means capable of producing a temperature rise inside the device and of melting said encapsulation means encapsulating the cell marker.

21. The detection device according to claim 16, wherein said cell marker storage means consists of a reserve of liquid cell marker solution separate from the detection support and in that said detection device comprises means for conveying said cell marker from said storage means to said detection support.

22. The detection device according to claim 21, wherein said means for the controlled release of the cell marker includes at least one controlled-flow pump.

23. The detection device according to claim 16, wherein said optical imaging device has a depth of focus 0.5 mm.

24. The detection device according to claim 16, wherein said optical imaging device is based on a CMOS sensor camera.

25. The detection device according to claim 16, wherein said optical imaging device has a field of view of 25 mm*25 mm.

26. The detection device according to claim 16, wherein said optical imaging device has a resolution at least 20 megapixels.

27. A detection support capable of being implemented in the detection method according to claim 1, wherein it comprises a rigid base through which passes at least one liquid feed line and at least one liquid aspiration and discharge line, said feed line being extended by a vent projecting from said base and passing through, on the one hand, a first orifice made in a rigid and permeable support means above said base and, on the other hand, a second orifice made in a flexible support disc made of glass fibres, said disc being positioned on said rigid and permeable support means and supporting a filtering membrane having a cut-off threshold comprised between 0.2 and 0.45 µm, capable of retaining microorganisms, said detection support further comprising a clamping ring fixed such that it is integral with said base and holding said base, said rigid and permeable support means, said support disc and said filtering membrane together.

* * * * *